United States Patent [19]

Denker

[11] Patent Number: 5,545,185

[45] Date of Patent: Aug. 13, 1996

[54] CARDIAC PACER WHICH COMPENSATES FOR EFFECTS OF ABRUPT CHANGES IN HEART RATE

[75] Inventor: Stephen Denker, 5240 N. Lake Dr., Whitefish Bay, Wis. 53217

[73] Assignee: Stephen Denker, Mequon, Wis.

[21] Appl. No.: 363,139

[22] Filed: Dec. 23, 1994

[51] Int. Cl.⁶ .................................................. A61N 1/365
[52] U.S. Cl. ........................................................... 607/14
[58] Field of Search ........................................ 607/14, 4, 9

[56] References Cited

U.S. PATENT DOCUMENTS

| | | | |
|---|---|---|---|
| 4,163,451 | 8/1979 | Lesnick et al. | 607/14 |
| 4,408,606 | 10/1983 | Spurrell et al. | 607/14 |
| 4,554,922 | 11/1985 | Prystowsky et al. | 607/14 |
| 4,577,633 | 3/1986 | Berkovots et al. | 128/419 |
| 4,750,494 | 6/1988 | King | 128/419 |
| 4,830,006 | 5/1989 | Haluska et al. | 607/4 |
| 4,880,005 | 11/1989 | Pless et al. | 607/14 |
| 4,941,471 | 7/1990 | Mehra | 128/419 |
| 4,998,974 | 3/1991 | Aker | 128/419 |
| 5,014,696 | 5/1991 | Mehra | 128/419 |
| 5,042,497 | 8/1991 | Shapland | 128/696 |
| 5,063,928 | 11/1991 | Grevis et al. | 128/419 |
| 5,144,947 | 9/1992 | Wilson | 128/419 |
| 5,181,511 | 1/1993 | Nickolls et al. | 128/419 |
| 5,188,105 | 2/1993 | Keimel | 128/419 |
| 5,203,326 | 4/1993 | Collins | 128/419 |
| 5,213,098 | 5/1993 | Bennett et al. | 128/419 |
| 5,275,621 | 1/1994 | Mehra | 607/5 |
| 5,292,339 | 3/1994 | Stephens et al. | 607/15 |
| 5,383,910 | 1/1995 | Den Dulk | 607/14 |
| 5,411,531 | 5/1995 | Hill et al. | 607/14 |
| 5,486,198 | 1/1996 | Ayers et al. | 607/4 |

OTHER PUBLICATIONS

Stephen Denker et al. "Facilitation of macrorenetry within the His–Purkinje system with aburpt changes in cycle length" Circulation, Jan. 1984.

Stephen Denker et al. "Divergence between refractoriness of His–Purkinje system and ventricular muscle with aburpt changes in cycle length" Circulation, Dec. 1983.

*Primary Examiner*—William E. Kamm
*Assistant Examiner*—Kennedy J. Schaetzle
*Attorney, Agent, or Firm*—Quarles & Brady

[57] ABSTRACT

Clinical studies of heart patients have demonstrated that ventricular tachyarrhythmia often is preceded by a foreshortened cardiac cycle length followed by a relatively long compensatory pause, thus producing in an abrupt short-to-long cycle length change. An implantable apparatus for preventing tachyarrhythmia measures the cardiac cycle length and detects the occurrence of a foreshortened cardiac cycle length more than a predefined amount between consecutive cycles. When a normal heart beat does not occur within a predefined period of time after such an abrupt change in cycle length, the resulting compensatory pause is eliminated by a cardiac pacer applying an appropriately timed electrical pulse to produce a contraction of the heart. The apparatus also includes a defibrillator to shock the heart in the event that the preventive pacing is not effective.

19 Claims, 2 Drawing Sheets

CARDIAC PACER WHICH COMPENSATES FOR EFFECTS OF ABRUPT CHANGES IN HEART RATE

BACKGROUND OF THE INVENTION

The present invention relates to implantable medical devices which deliver energy to cardiac tissue in an attempt to restore a normal sinus rhythm to a patient.

Tachycardia refers to any fast, abnormal rhythm of the heart which may be amenable to treatment by electrical discharges. One form of tachycardia is referred to as ventricular tachyarrhythmia (VTA). A common therapy for treating VTA is to implant a cardiac pacer/defibrillator in the patient, Cardiac pacers traditionally have been used to detect a slow heart rate and in response discharge electrical energy into the heart tissue at a faster pace which increases the heart rate. Pacing technology also can respond to the detection of arapid heart rate by producing rapid pacing which terminates the tachycardia and thereby causing the heart rate to return to normal. This present cardiac pacing technology is not specifically designed to reduce the occurrence of ventricular tachyarrhythmia, but rather to terminate the condition after it occurs.

However, rapid pacing techniques can accelerate and worsen the arrhythmias in some instances. As a consequence, cardiac pacers that treat rapid heart rates do so in conjunction with an implantable cardioverter defibrillator (ICD). The cardioverter defibrillator detects rapid ventricular tachyarrhythmias that do not respond to rapid pacing and employs cardioversion/defibrillation to terminate the arrhythmia.

Clinical studies have demonstrated that abrupt short to long changes in the ventricular cycle length often preceded and possibly precipitated ventricular tachyarrhythmia. The ventricular cycle length, i.e. the period between ventricular contractions, normally remains relatively constant and varies only gradually, even upon the commencement of strenuous exercise. However, occasionally a premature ventricular contraction occurs in the form of a spurious pulse from a muscle cell which disrupts the normal electrical pulse pattern in the heart. Because the heart tissue often does not recover from an early beat in time to conduct the next regular electrical pulse, the subsequent normal heartbeat does not occur. Thus, the heart undergoes very rapid beat followed by a significantly longer compensatory pause before a subsequent beat occurs. As a result, the heart is subjected to a very fast heart rate which quickly changes to a very slow rate. Such rapid rate change significantly intensifies dispersion of refractoriness in patients who already have other causes of increased dispersion of refractoriness, such as damaged ventricular myocardium from a myocardial infarction or cardiomyopathy. A premature ventricular contraction may facilitate tachyarrhythmia in these patients.

SUMMARY OF THE INVENTION

A general object of the present invention is to provide an antitachycardia therapy device which detects a premature heartbeat followed by a resulting long pause and responds with corrective action to restore a normal heart rate by preventing the pause. This decreases dispersion and thereby lowers the incidence of VTA.

Another object is to electrically stimulate the heart to shorten the compensatory pause and thus reduce the severity of the short-to-long change in cardiac cycle length.

A further object of the present invention is to provide such functionality in an implantable cardiac pacer/defibrillator.

Yet another object is to enable the treatment initiation criteria to be programmable so that the operation of the antitachycardia therapy device may be configured for each particular patient.

These objects are satisfied by an apparatus that detects the occurrence of a very short cardiac cycle length followed by a long compensatory pause and responds by pacing the heart for one or several beats until a relatively constant rate is restored. The apparatus measures the cardiac cycle lengths and detects significantly premature heart beats by sensing abrupt changes heart cycles. When a heart beat fails to occur within a predefined time period after a significantly premature heart beat, cardiac pacing is initiated. For example, a series of electrical pulses are applied to produce contractions of the heart, until a normal heart beat occurs between the pulses.

In the preferred embodiment of this apparatus, a mechanism is provided for a physician to select a threshold value for the cardiac cycle length change, and the predefined time period before initiating the cardiac pacing technique.

This technique responds, to a ratio of two consecutive cycle lengths exceeding a defined magnitude as a precursor of ventricular tachyarrhythmia, by initiating pacing treatment. This is in contrast to conventional cardiac pacing which merely is responsive the heart rate slowing to below a set threshold level. Furthermore, conventional cardiac pacing responds by applying stimulating electrical pulses at a constant rate to produce heart beats at a constant cycle length and does not address preventing the onset of tachyarrhythmia.

DETAILED DESCRIPTION OF THE INVENTION

Figure 1:
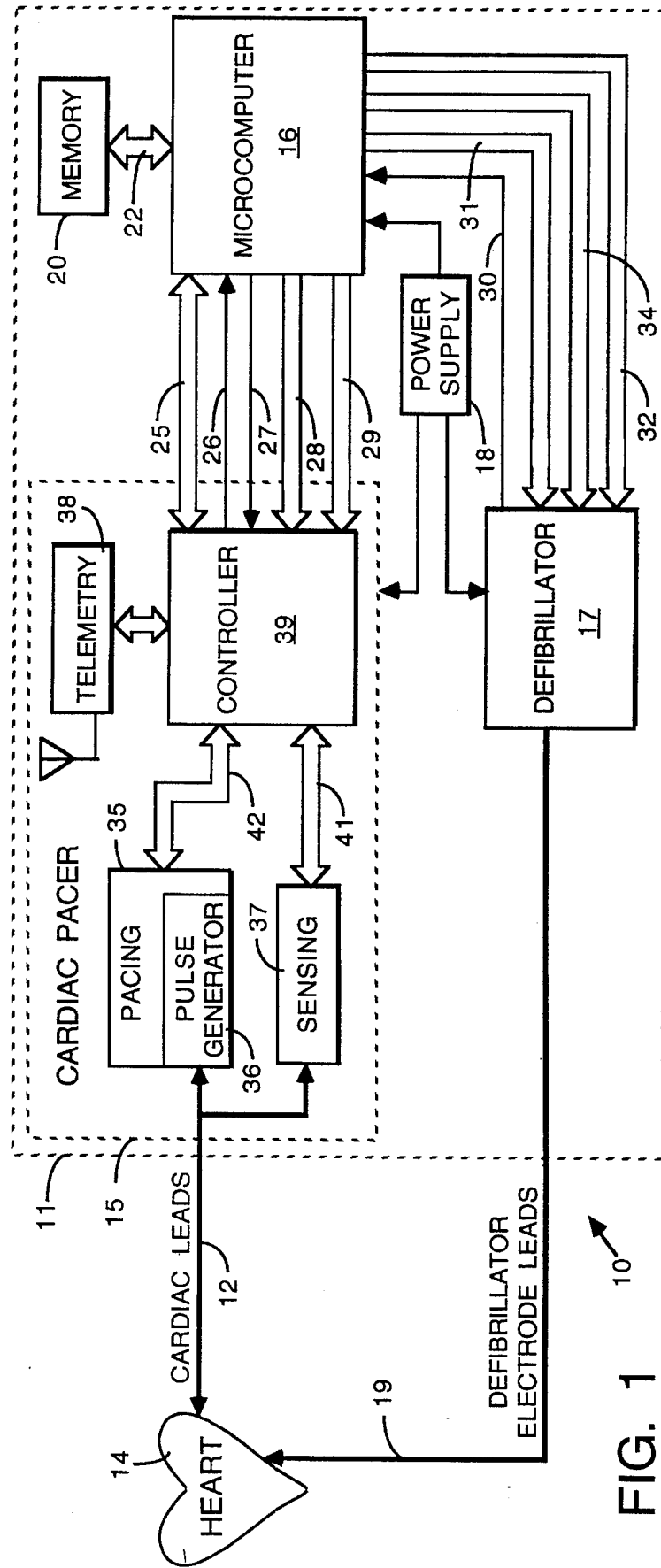
FIG. 1 is a block diagram of an antitachycardia system which includes a cardiac pacer and a defibrillator.

Referring to FIG. 1, an arrhythmia control system 10 is designed to be implantable and includes a pulse module 11 of a conventional hardware design. The pulse module 11 comprises a cardiac pacer 15, a microcomputer 16, a defibrillator 17 and a power supply 18. Cardiac leads 12 connect the cardiac pacer 15 to the patient's heart 14 for the detection of analog signals representing cardiac electrical activity and for the delivery of pacing pulses to the heart. The cardiac pacer 15 comprises pacing circuit 35 which includes a pacing pulse generator 36, sensing circuit 37, and telemetry circuit 38. In addition, there is a controller 39 which includes an interface to microcomputer 16.

The microcomputer 16 responds to signals received from cardiac pacer 15 as well as from defibrillator 17 by performing operations which generate different control and data output signals for both the cardiac pacer and the defibrillator. The defibrillator 17 produces a high voltage to charge its capacitors and then discharges them in response to control signals from microcomputer 16. Defibrillator electrode leads 19 transfer the energy of a defibrillator charge from the implanted pulse module to the heart 14.

As more fully described below, the microcomputer 16 is connected to an external memory 20 by an address and data bus 22 for the storage of data. Microcomputer 16 and cardiac pacer 15 are connected by a communication bus 25, a sense line 26, a pace control line 27, a sensitivity control bus 28, and a pacing energy control line 29. The microcomputer 16 is connected to defibrillator 17 by a charge level line 30, a charge control bus 31, a shock control bus 32, and a dump control bus 34.

In operation, a conventional sensing circuit 37 detects analog signals from the heart 14 and converts the detected signals to digital signals. Furthermore, sensing circuit 37 receives an input sensing control signal (which determines the sensitivity of the detection circuits in the sensing circuit) via a sense control bus 41 from controller 39. A change in this sensitivity affects the voltage deviation required at the sensing electrode for a sensed event to be registered.

Pacing circuit 35 also receives inputs from controller 39 including a pace control signal and a pacing energy control signal by way of pacing control bus 42 which carries the signals that arrive at the controller over pace control line 27 and pacing energy control bus 29. The pace control signal determines the type of pacing to occur while the magnitude of the pulse energy is determined by the pacing energy control signal. Pacing circuit 35 causes pulse generator 36 to generate the pacing pulse 44 which is delivered to the patient's heart 14 by means of cardiac leads 12.

Telemetry circuit 38 provides a bi-directional signal interface between the controller 39 of the cardiac pacer 15 and a conventional external programmer (not shown). The signals are sent between the telemetry circuit 38 and the external programmer by inductive or RF coupling thereby enabling reprogramming and recovery of data from the pulse module 11 after implantation. This interface forwards commands from the programmer to the controller 39 allowing operating parameters of the cardiac pacer 15 to be altered. Communications bus 25 carries other commands from the external programmer to microcomputer 16 to configure operation of defibrillator 17. As in previous pacing devices operational and physiological data stored in the memory can be sent to the external programmer via the telemetry circuit 38 so that the cardiologist can monitor the patient and performance of the arrhythmia control system 10.

Appropriate telemetry commands also cause the telemetry circuit 38 to transmit cardiac function information and other data from the pulse module !1 to the external programmer. Stored data is read out by microcomputer 16 and sent via communications bus 25, through controller 39 in cardiac pacer 15 and into telemetry circuit 38 for transmission to the external programmer.

Referring still to FIG. 1, the microcomputer 16 includes a microprocessor, timers, I/O circuits, random access memory (RAM) and read only memory (ROM). The internal RAM acts as a scratch pad memory and active memory during execution of software programs and routines stored in internal ROM. This software includes system supervisory programs and detection algorithms, as well as programs for storing in external memory 20 data concerning the functioning of module 11 and the electrogram provided by cardiac leads 12. The interval hardware timers implement some timing functions required by microcomputer 16 without resorting to software, thus reducing computational loads on and power dissipation by the microprocessor.

Microcomputer 16 receives various status and/or control signals from cardiac pacer 15 and defibrillator 17. During normal pacing operations, a sense signal on sense line 26 from the cardiac pacer 15 is used by microcomputer 16 to perform operations such as arrhythmia detection. The microcomputer 16 produces output signals such as a pace signal on pace control line 27 which determines the type of pacing to occur. Other cardiac pacer control output signals generated by microcomputer 16 include an energy signal on pacing energy control bus 29 which determines the magnitude of the pulse energy, and a sensitivity signal on control bus 28, which determines the sensitivity setting of the sensing circuit 37.

The microcomputer 16 provides the defibrillator 17 with a shock signal on shock control line 32 which instructs that a shock is to be delivered to the patient, a charge signal on charge control bus 31 which determines the voltage level of the shock, and a dump signal on dump control line 34 which indicates that a capacitor charge is to be dumped to an internal load within defibrillator 17. Charged voltage level line 30 provides a digital signal representative of charge voltage from an analog to digital converter within defibrillator 17, thus providing a feedback loop which assures that a shock of a proper energy level is delivered by defibrillator 17.

Figure 2A:
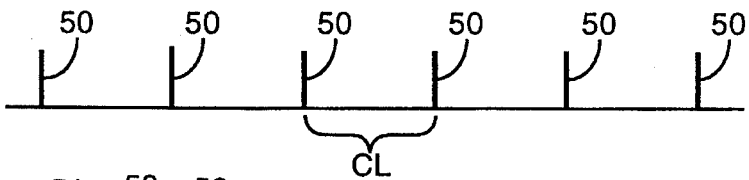
FIG. 2A depicts several heartbeats having a normal rhythm.

In addition to being programmed to perform conventional heart pacing and defibrillation functions, additional routines are stored within the internal ROM of the microcomputer 16 which carry out the novel tachycardia prevention technique of the present invention. This technique is graphically depicted in FIGS. 2A–2C which represent several heartbeats during different conditions of the patient. Specifically, FIG. 2A depicts a normal heart rate with each beat 50 occurring at relatively constant cardiac cycle lengths (CL). As noted previously, even when an individual commences strenuous exercises, the heart rate and therefore the cardiac cycle length changes in a relatively gradual manner. Thus, a sudden, significant change in cardiac cycle length indicates an abnormal condition.

Figure 2B:
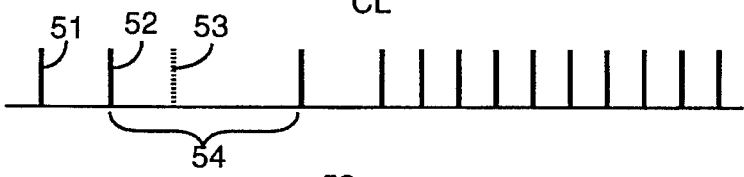
FIG. 2B depicts several heartbeats which include a premature beat.

The heartbeat pattern depicted in FIG. 2B commences with a normal heartbeat 51 followed by a premature heartbeat 52 occurring before the point at which a normal heartbeat, indicated by dashed line 53 would occur. Because the conductive tissue of the heart does not recover immediately following the premature beat 52, when the next normal beat 53 is to occur, the electrical conduction is impeded and the normal heartbeat 53 does not occur. Thereafter, a relatively long pause denoted by interval 54 occurs, thus presenting the heart with a relatively short cycle length between beats 51 and 52 followed by a much longer quiet period 54. Thus, the heart is subjected in effect to a very rapid heart rate followed by a significantly slower heart rate. As discussed previously, this abrupt, rapid to slow heart rate transition often precedes tachycardia. As a consequence, the heart beats occurring after the premature beat 52 are very rapid, representing VTA.

The novel software routine added to the programming of the microcomputer 16 detects the heart rate going from rapid to slow within one beat and initiates a pacing technique which restores the normal heart rhythm and avoids the onset of tachycardia.

Figure 3:
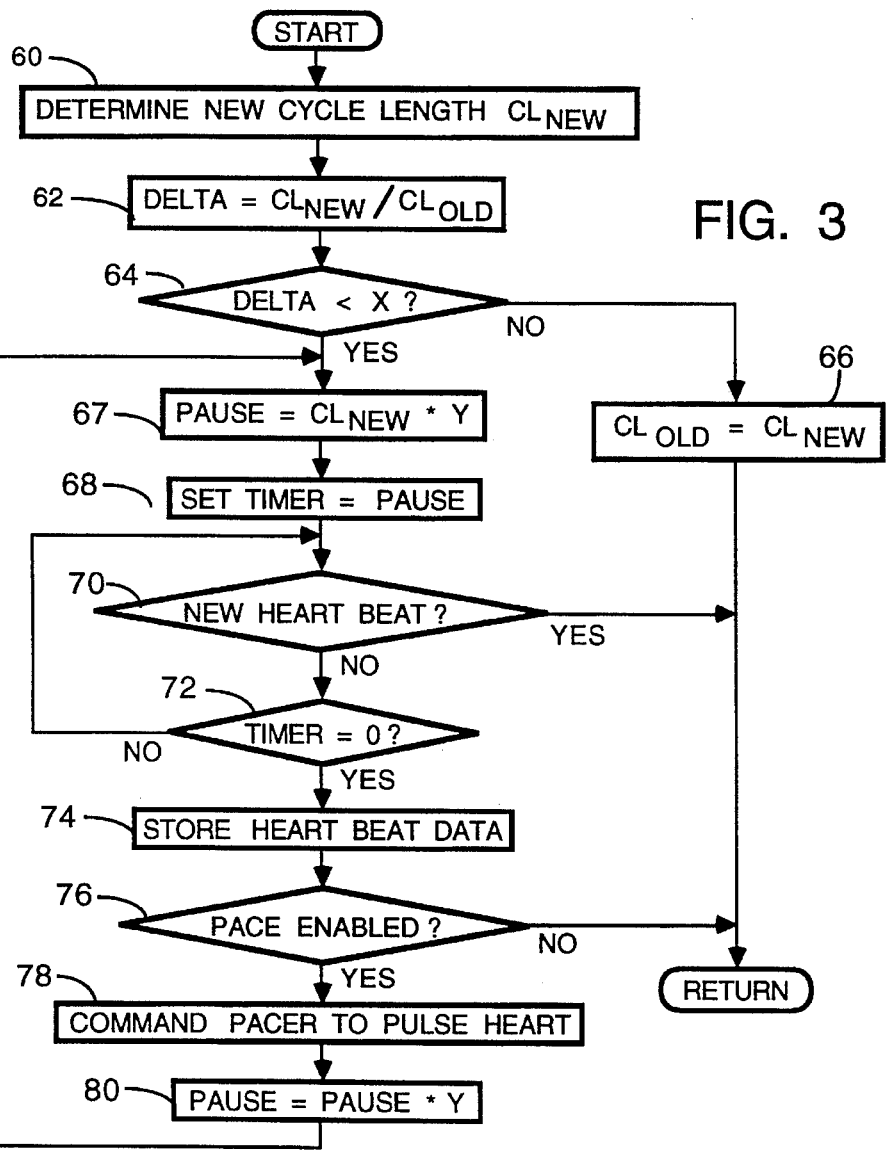
FIG. 3 represents a flowchart of a software routine which is programmed into a cardiac pacer/defibrillator to perform antitachycardia therapy according to the present invention.

When the conventional software within the pulse module 11 detects a heartbeat, one of the routines stored within the ROM of microcomputer 16 that is called is depicted by the flowchart of FIG. 3. This routine commences at step 60 where microcomputer 16 determines the new cardiac cycle length ($CL_{NEW}$) by reading one of the internal timers of the microcomputer that is used to measure the interval between heartbeats. Then at step 62, the value of variable DELTA is computed by dividing the value of $CL_{NEW}$ with the value of the previously measured cardiac cycle length, $CL_{OLD}$. The value of DELTA represents the change in cardiac cycle length from one ventricular period to the next period. Next, the microcomputer 16 determines whether the newly computed value of DELTA is below a threshold value X which indicates prematurity. The value of X can be varied from patient to patient and is programmed by the cardiologist via an external programmer and telemetry circuitry 38 when the pulse module 11 is implanted or anytime thereafter. For example, DELTA may have a value of 0.80. If DELTA exceeds the threshold value, the new beat was not sufficiently premature to require intervention by the arrhythmia control system 10, and the program execution branches to step 66 where the value of $CL_{OLD}$ is set to the new cycle length value $CL_{NEW}$ before returning to the main system program of the cardiac pacer 15.

Figure 2C:
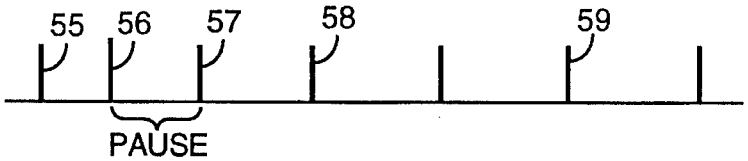
FIG. 2C depicts heartbeats which occur in a condition similar to FIG. 2B, but where the heart is treated with a device according to the present invention.

However, if at step 64 the value of DELTA is found to be below the threshold value X, a determination is made by the microcomputer 16 that a significantly premature heartbeat has occurred. For example, as shown in FIG. 2C, after a regular heartbeat 55, a premature heartbeat 56 occurs producing a value for DELTA which is less than the threshold value. In response to this occurrence, the software routine branches from step 64 to step 67 where the microcomputer 16 derives a value for a variable designated PAUSE which determines how long to wait for a regular heart beat to occur before initiating corrective treatment. The value of PAUSE is computed by multiplying the new cycle length $CL_{NEW}$ by Y, where Y is a value programmed by the cardiologist and may be varied from patient to patient. Typically, Y has a value greater than one (e.g. 1.2) so that the apparatus will wait for at least as long as the new cycle length. At step 68, an internal timer of the microcomputer is initialized with the value of PAUSE.

The microcomputer 16 checks for the occurrence of a spontaneous heartbeat at step 70. A spontaneous heartbeat is a heartbeat produced by the heart, as opposed to a heartbeat produced by an electrical pulse from the cardiac pacer 15. Should another spontaneous heartbeat occur before the timer elapses, that is a heartbeat occurs before the expiration of the interval defined by the variable PAUSE, the execution by the microcomputer 16 returns to the main system program of the pulse module 11. Thus, if the heart resumes a normal rhythmic pattern, the treatment provided by the software routine in FIG. 3 is aborted. There may be several rapid heart beats before a compensatory pause occurs, in which case the software routine will terminate after each beat until the compensatory pause is detected.

However if a normal spontaneous heartbeat has not occurred, the value of the timer is checked by the microcomputer 16 at step 72 to determine whether it has elapsed, as occurs at the end of the interval defined by PAUSE. If the timer has not elapsed, the program execution returns to step 70. This loop of checking for a spontaneous heartbeat or the elapse of the timer continues until one of those two events takes place.

If the heart does not return to normal rhythm following a premature beat, that is a normal spontaneous heartbeat does not occur within the PAUSE interval, an indication that the defined short to long cycle length sequence has occurred is stored in memory 22 at step 74. Then at step 76, a determination is made whether antitachycardia prevention pacing has been enabled. The arrhythmia control system 10 may first be configured simply to detect and record the occurrence of each short to long cycle length sequence. This information can be read from the system so that a cardiologist can determine whether that sequence precedes tachycardia in this patient and thus whether the patient will benefit from the antitachycardia prevention pacing. If such benefit would be derived, the cardiologist then can enable system 10 to stimulate the heart following subsequent short to long cycle length sequence occurrences.

When the pulsing is found enabled at step 76, microcomputer 16 commands the cardiac pacer 15 to stimulate the heart with a pulse of electricity at step 78. For example, if a another spontaneous heartbeat would not occur until interval 54 shown in FIG. 2B and that interval is greater than the PAUSE time, the cardiac pacer 15 will apply an electrical pulse to the heart through cardiac leads 12 in a conventional manner to produce a heartbeat 57 as shown in FIG. 2C.

Then the variable PAUSE is increased by multiplying its present value by Y at step 80. Thereafter execution of the software routine by microcomputer 16 returns to step 68 where the timer is re-initialized with the new value of PAUSE. If a normal, or spontaneous, heartbeat does not occur before the timer elapses again, another pulse of electricity is applied to the heart to stimulate a heartbeat 58. Thus upon each loop through the pulsing routine the waiting period determined by PAUSE is lengthened, which also increases the interval between electrical pulses applied by the cardiac pacer 15 to the heart. This process continues to apply pulses to generate heartbeats until a normal spontaneous heartbeat 59 occurs during a PAUSE interval.

When a spontaneous heartbeat occurs, the program execution returns to the main software program for the pulse module 11. Alternatively, several normal spontaneous heartbeats may be required to occur before the antitachyarrhythmia routine depicted in FIG. 3 returns to the normal operation of the pulse module, thus ensuring that the heart has returned to a normal rhythm.

I claim:

1. A method of preventing tachycardia comprising the steps of:

selecting threshold value for a change in heart cycle length from one heart cycle to a subsequent heart cycle;

selecting a time period, which is longer than the subsequent heart cycle;

measuring heart cycle lengths of an animal;

deriving a change in the heart cycle length from one heart cycle to a subsequent heart cycle;

comparing the change in the heart cycle length to the threshold value to detect when the heart cycle length decreases;

detecting when a new heart beat fails to occur within the time period which commences after the subsequent heart cycle;

if a new heart beat fails to occur within the time period after the change in heart cycle length exceeds the threshold value, commence treating the animal with a cardiac pacing technique to prevent tachycardia from occurring.

2. The method as recited in claim 1 wherein the step of deriving derives a change in heart cycle length between two consecutive heart cycles.

3. The method as recited in claim 1 wherein the cardiac pacing technique comprises applying an electrical pulse to a heart of the animal.

4. The method as recited in claim 1 wherein the cardiac pacing technique comprises:

applying an electrical pulse to a heart of the animal; and applying subsequent electrical pulses to the heart of the animal whenever a heart beat fails to occur within the time period following a preceding electrical pulse.

5. The method as recited in claim 1 wherein the cardiac pacing technique comprises:

applying an electrical pulse to a heart of the animal; and thereafter a) increasing the time period to an increased time period;

b) applying a subsequent electrical pulse to the heart of the animal if a heart beat fails to occur within the increased time period.

6. The method recited in claim 5 wherein steps (a) and (b) are repeated until at least one spontaneous heart beat occurs.

7. The method as recited in claim 1 further comprising applying cardioversion/defibrillation to the animal, if after the a cardiac pacing technique, the animal fails have a normal heart rate.

8. The method as recited in claim 2 wherein a determination is made that the change in heart rate cycle length exceeds the threshold value when the subsequent heart cycle has a length which is 80 percent or less of a length of the one heart cycle.

9. The method as recited in claim 1 wherein comparing the change in the heart cycle length determines when the subsequent heart cycle length is shorter than the one heart cycle.

10. The method as recited in claim 1 wherein the time period is at least 1.2 times a length of the subsequent heart cycle.

11. The method as recited in claim 1 wherein the step of selecting a time period comprises multiplying a length of the subsequent heart cycle by a value that is greater than one.

12. The method as recited in claim 11 wherein the value is at least 1.20.

13. An apparatus for preventing tachycardia in a heart of an animal, said apparatus comprising:

a cardiac pacer which responds to a control signal by applying an electrical pulse to the animal to contract the heart;

a mechanism that measures the cardiac cycle length;

a detector coupled to said mechanism to produce a first indication when the cardiac cycle length decreases more than a predefined amount from one cycle to a subsequent cycle;

a processor which responds to the first indication by producing a second indication when a new heart beat fails to occur within a predefined time period after the subsequent cycle, where the predefined time period is longer than the subsequent cycle; and an evaluator that responds to the second indication by sending the control signals to the cardiac pacer to perform a cardiac pacing technique to prevent tachycardia from occurring.

14. The apparatus as recited in claim 13 further comprising a telemetry circuit for altering the predefined amount.

15. The apparatus as recited in claim 13 further comprising a telemetry circuit for altering the predefined period of time.

16. The apparatus as recited in claim 13 further comprising a defibrillator which is responsive to said evaluator for applying a shock to the heart if a normal heart rhythm fails to occur after a given number of electrical pulses are applied by said cardiac pacer.

17. A method of preventing tachycardia comprising:

measuring a first length of a first heart cycle;

measuring a second length of a second heart cycle which occurs after the first heart cycle;

determining when the second length is shorter than the first length by at least a predefined amount;

deriving a time period as a function of the second length, where the time period is longer than the second length;

detecting when a new heart beat fails to occur within the time period following the second heart cycle and in response thereto producing an indication of such occurrence; and responding to the indication by commencing treatment of the animal with a cardiac pacing technique to prevent tachycardia from occurring.

18. The method as recited in claim 17 wherein the second heart cycle consecutively follows the first heart cycle.

19. The method as recited in claim 17 wherein the cardiac pacing technique comprises:

(a) applying an electrical pulse to a heart of the animal; and thereafter (b) increasing the time period to an increased time period;

(c) applying a subsequent electrical pulse to the heart of the animal if a heart beat fails to occur within the increased time period; and (d) repeating steps (b) and (c) until at least one spontaneous heart beat occurs.

* * * * *